US011191228B2

(12) United States Patent
Tolla et al.

(10) Patent No.: US 11,191,228 B2
(45) Date of Patent: Dec. 7, 2021

(54) WATERMELON WITH IMPROVED PROCESSING QUALITIES

(71) Applicant: Seminis Vegetable Seeds, Inc., St. Louis, MO (US)

(72) Inventors: Greg Tolla, Woodland, CA (US); Benito Juarez, Davis, CA (US); Fred McCuistion, Tifton, GA (US)

(73) Assignee: Seminis Vegetable Seeds, Inc., St. Louis, MO (US)

(*) Notice: Subject to any disclaimer, the term of this patent is extended or adjusted under 35 U.S.C. 154(b) by 608 days.

(21) Appl. No.: 15/241,260

(22) Filed: Aug. 19, 2016

(65) Prior Publication Data

US 2016/0353682 A1 Dec. 8, 2016

Related U.S. Application Data

(63) Continuation of application No. 12/856,286, filed on Aug. 13, 2010, now Pat. No. 9,420,753, which is a continuation of application No. 10/972,190, filed on Oct. 22, 2004, now Pat. No. 9,173,356.

(60) Provisional application No. 60/584,964, filed on Jul. 2, 2004.

(51) Int. Cl.
*A01H 1/02* (2006.01)
*A01H 5/08* (2018.01)
*A01H 1/00* (2006.01)
*A01H 3/04* (2006.01)

(52) U.S. Cl.
CPC .......... *A01H 5/08* (2013.01); *A01H 1/00* (2013.01); *A01H 1/02* (2013.01); *A01H 3/04* (2013.01)

(58) Field of Classification Search
CPC .......... A01H 5/08; A01H 1/02; A01H 1/00
USPC ........................... 800/260, 269, 308
See application file for complete search history.

(56) References Cited

U.S. PATENT DOCUMENTS

| | | | |
|---|---|---|---|
| 5,866,764 A | 2/1999 | Gabor et al. | |
| 6,096,944 A | 8/2000 | Vierling et al. | |
| 6,207,367 B1 | 3/2001 | Helentjaris et al. | |
| 6,399,855 B1 | 6/2002 | Beavis | |
| 6,414,226 B1 | 7/2002 | Hoogstraten | |
| 6,639,132 B1 | 10/2003 | Duvick et al. | |
| 6,670,530 B2 | 12/2003 | Eby et al. | |
| 9,173,356 B2 * | 11/2015 | Tolla et al. | A01H 5/08 800/308 |
| 2003/0172412 A1 | 9/2003 | Zhang et al. | |
| 2005/0015827 A1 | 1/2005 | Podlich et al. | |
| 2005/0204780 A1 | 9/2005 | Moridaira et al. | |
| 2005/0216545 A1 | 9/2005 | Aldrich et al. | |
| 2005/0218305 A1 | 10/2005 | Tsukamoto et al. | |
| 2006/0005284 A1 | 1/2006 | Tolla et al. | |
| 2009/0031438 A1 | 1/2009 | Kennard et al. | |
| 2010/0306883 A1 | 12/2010 | Tolla et al. | |
| 2013/0055466 A1 | 2/2013 | Juarez et al. | |
| 2015/0101072 A1 | 4/2015 | Lanini | |

FOREIGN PATENT DOCUMENTS

| | | |
|---|---|---|
| WO | WO 03/051103 A2 | 6/2003 |
| WO | WO 03/096798 A1 | 11/2003 |

OTHER PUBLICATIONS

Leskovar et al, Acta Hort. 628, ISHS 2003, pp. 147-151.*
Bang et al, Journal of Horticultural Science, 2004, 76 (6) 885-890.*
Kano, 2004, J. Hort. Sci. Biotechnol. 79:142-145.*
Buttrose et al, 1978, Ann. Bot. 42:599-608.*
Risse et al (J. Amer. Soc. Hort. Sci. 1990, 115(3): 440-443).*
Crall et al (Soil and Crop Sci. Soc. Fla. Proc 4, 1986 132-134).*
Karchi et al (Hassadeh, 1981, 61:1284-1285).*
Nerson et al (Hassadeh, 1982 62:606-607).*
Karchi et al, 1981a, Hassadeh 61:1284-1285.*
Crall et al (HortScience 29(6): 707-708, 1994).*
Crall (HortScience 25(7): 812-813, 1990).*
Abstracts of the ASHS Southern Region 50th Annual Meeting, *HortScience*, 25(8):848-865 (1990).
Alkridge et al., Spring 2009 and 2010 Commercial Fruit and Vegetable Variety Trials, Regional Bulletin 22, Alabama's Agricultural Experiment Station, Auburn University, pp. 1-32 (2011).
Andrus et al., "Production of Seedless Watermelons," *Agricultural Research Service*, USDA Technical Bulletin No. 1425, pp. 1-15 (1971).
Articles about US Seedless Watermelons, *US Seedless Press*, pp. 1-3 (1999) <http://www.usseedless.com/press/htm>.
Bang et al., "Deficit irrigation impact on lycopene, soluble solids, firmness and yield of diploid and triploid watermelon in three distinct environments," *Journal of Horticultural Science*, 79(6):885-890 (2004).
Bang, "Environmental and Genetic Strategies to Improve Carotenoids and Quality in Watermelon," Ph.D. Thesis, Texas A&M University, pp. 1-127 (2005).
Buttrose et al., "Some Effects of Light Intensity, Daylength and Temperature on Growth of Fruiting and Non-fruiting Watermelon (*Citrullus lanatus*)," *Ann. Bot.*, 42:599-608 (1978).
Cartaxo et al., "Controlled Atmosphere Storage Suppresses Microbial Growth on Fresh-Cut Watermelon," *Proc. Fla. State Hort. Soc.*, 110:252-257 (1997).
Chen et al., "Gene Transfer Via Pollen-Tube Pathway for Anti-Fusarium Wilt in Watermelon," *Biochemistry and Molecular Biology International*, 46(6):1201-1209 (1998).
Crall et al., "Florida 'Icebox' Cultivars as a Factor in Watermelon Production in Florida and Other Producing States," *Soil and Crop Sci. Soc. Fla. Proc.*, 45:132-134 (1986).

(Continued)

*Primary Examiner* — Keith O. Robinson
(74) *Attorney, Agent, or Firm* — Arnold & Porter Kaye Scholer LLP; Alissa M. Eagle; David R. Marsh

(57) ABSTRACT

A watermelon plant that produces fruit having (i) ultra-firm flesh and/or liquid-retaining flesh and (ii) soluble solids of at least about 6 brix.

8 Claims, 2 Drawing Sheets

(56) References Cited

OTHER PUBLICATIONS

Crall et al., "SSDL: A High-quality Icebox Watermelon Breeding Line Resistant to Fusarium Wilt and Anthracnose," *HortScience*, 29(6):707-708 (1994).
Crall, "'Charlee' Watermelon," *HortScience*, 25(7):812-813 (1990).
Crall, "Fifty Years of Watermelon Breeding at ARC Leesburg," *Proc. Fla. State Hort. Soc.*, 94:156-158 (1981).
Eigsti, "Improvement of Watermelon with Polyploids," *Cucurbit Genetics Cooperative Report CGC2-15*, 2(article 15):25-26 (1979).
EMBL Online Database Accession No. CS490596, "Sequence 29 from Patent WO2007003397," pp. 1 (2007).
Extended European Search Report dated Jun. 15, 2012, as received in European Patent Application No. 12151233.9.
Extended European Search Report dated Mar. 25, 2015, as received in European Patent Application No. 12827082.4.
Extended European Search Report dated Sep. 14, 2009, as received in European Patent Application No. 05764293.6.
Fonseca et al., "Shock and Vibration Forces Influence the Quality of Fresh-Cut Watermelon," *Proc. Fla. State Hort. Soc.*, 112:147-152 (1999).
Gamborg, "Plant Tissue Culture, Biotechnology, Milestones.," *In Vitro. Cell. Dev. Biol. Plant*, 38:84-92 (2002).
Geneseq Online Database Accession No. ABH42851, "Oligonucleotide Seq ID No. 242828 for detecting SNP TSC0059263" (2002).
Gillies et al., "Cooling Method Influences the Postharvest Quality of Broccoli," *HortScience*, 30(2):313-315 (1995).
Gilreath et al., "Evaluation of Icebox Watermelon Cultivars in West Central and Southwest Florida," *Proc. Fla. State Hort. Soc.*, 99:331-334 (1986).
Griffith, "The Significance of Pneumococcal Types," *Journ. of Hyg.*, XXVII(2):114-159 (1928).
GRIN Online Database Accession No. Grif 15895, "Sugar Baby," pp. 1-2 (2003).
GRIN Online Database Accession No. PI 296341, "Tsamma," pp. 1-2 (1964).
GRIN Online Database Accession No. PI 635683, "Sweet Siberian," pp. 1-2 (1963).
Guner et al., "Gene List for Watermelon," *Cucurbit Genetics Cooperative Report*, 26:76-92 (2003).
Gunter et al., "Elongated Seedless Watermelon Cultivar Trials for Southwestern Indiana, 2003," Southwest Purdue Agricultural Program, Purdue University, pp. 1-2 (2003).
Gunter et al., "Evaluation of Non-Harvested Watermelon Pollenizers for Flowering Characteristics and *Fusarium oxysporum* fsp. *niveum* Susceptibility," Southwest Purdue Agricalatural Program, Purdue University, pp. 1-10 (2006).
Gunter et al., "Personal Sized Seedless Watermelon Cultivar Trials for Southwestern Indiana, 2004," Southwest Purdue Agricultural Program, Purdue University, pp. 1-2 (2004).
Gunter et al., "Personal Sized Seedless Watermelon Cultivar Trials for Southwestern Indiana, 2005," Southwest Purdue Agricultural Program, Purdue University, pp. 1-2 (2005).
Gunter et al., "Seeded Watermelon Cultivar Trials for Southwestern Indiana, 2003," Southwest Purdue Agricultural Program, Purdue University, pp. 1-2 (2003).
Gunter et al., "Seeded Watermelon Cultivar Trials for Southwestern Indiana, 2004," Southwest Purdue Agricultural Program, Purdue University, pp. 1-2 (2004).
Gunter et al., "Seeded Watermelon Cultivar Trials for Southwestern Indiana; 2005," Southwest Purdue Agricultural Program, Purdue University, pp. 1-2 (2005).
Gunter et al., "Seeded Watermelon Cultivar Trials for Southwestern Indiana, 2001," Southwest Purdue Agricultural Program, Purdue University, pp. 1-2 (2001).
Gunter et al., "Seedless Watermelon Cultivar Trials for Southwestern Indiana, 2007," Department of Horticulture Science, North Carolina State University, pp. 1-8 (2007).
Gunter et al., "Seedless Watermelon Cultivar Trials for Southwestern Indiana, 2001," Southwest Purdue Agricultural Program, Purdue University, pp. 1-2 (2001).
Gunter et al., "Seedless Watermelon Cultivar Trials for Southwestern Indiana, 2003," Southwest Purdue Agricultural Program, Purdue University, pp. 1-2 (2003).
Gunter et al., "Seedless Watermelon Cultivar Trials for Southwestern Indiana, 2004," Southwest Purdue Agricultural Program, Purdue University, pp. 1-3 (2004).
Gunter et al., "Seedless Watermelon Cultivar Trials for Southwestern Indiana, 2006," Southwest Purdue Agricultural Program, Purdue University, pp. 1-4 (2006).
Gunter et al., "Seedless Watermelon Cultivar Trials for Southwestern Indiana, 2005," Southwest Purdue Agricultural Program, Purdue University, pp. 1-3 (2005).
Gusmini et al., "Rind Thickness of Watermelon Cultivars for Use in Pickle Production," *HortTechnology*, 14(4):540-545 (2004).
Gusmini, "Watermelon (*Citrullus lanatus*) Breeding Handbook," North Carolina State University, Raleigh, NC, pp. 1-90 (2003).
Hashizume et al., "Construction of a linkage map and QTL analysis of horticultural traits for watermelon [*Citrullus lanatus* (THUNB.) Matsum & Nakai] using RAPD, RFLP and ISSR markers," *Theor. Appl. Genet.*, 106:779-785 (2003).
Hawkins et al., "Linkage Mapping in a Watermelon Population Segregating for Fusarium Wilt Resistance," *J. Amer. Soc. Hort. Sci.*, 126(3):344-350 (2001).
Henderson et al., "Interaction of Flesh Color Genes in Watermelon," *Journal of Heredity*, 89(1):50-53 (1998).12/856,286.
Henderson, "Inheritance of Orange Flesh Color in Watermelon," *Cucurbit Genetics Cooperative Report CGC12-26*, 12(article 26):59-63 (1989).
Holmes et al., "Cucurbitaceae 2006 Proceedings," *Universal Printing & Publishing*, Raleigh, NC, pp. 1-602 (2006).
Hybrid Watermelon, *Jeffreys Seed Company Online: Vegetable Seed Catalog*, pp. 1-4, n.d., Web, Mar. 30 2004 <http://www.jeffreysseed.com/vegetable_seed/watermelon_02.html>.
International Preliminary Report on Patentability dated Mar. 10, 2009, as received in International Application No. PCT/US2005/023902.
International Preliminary Report on Patentability dated Mar. 4, 2014, as received in International Application No. PCT/US2012/053476.
International Search Report dated Apr. 9, 2008, as received in International Application No. PCT/US2005/023902.
International Search Report dated Jan. 25, 2013, as received in International Application No. PCT/US2012/053476.
Jaskani et al., "Comparative study on vegetative, reproductive and qualitative traits of seven diploid and tetraploid watermelon lines," *Euphytica*, 145:259-268 (2005).
Kang et al., "Inheritance of Lobed Leaf, Plant Shape, and Sugar Content in Watermelon (*Citrullus lanatus* (Thunb.) Matsum. et. Nakai)," *Korean J. Breed.*, 32(4):315-316 (2000).
Kano, "Effects of summer day-time temperature on sugar content in several portions of watermelon fruit (*Cirtrullus lanatus*)," *J. Hort. Sci. Biotechnol.*, 79(1):142-145 (2004).
Karakurt et al., "Cell wall-degrading enzymes and pectin solubility and depolymerization in immature and ripe watermelon (*Citrullus lanatus*) fruit in response to exogenous ethylene," *Physiologia Plantarum*, 116:398-405 (2002).
Karchi et al., "'Alena' Watermelon," *HortScience*, 16(4):573 (1981).
Karchi et al., "Alena" Watermelon: A Quality Cultivar for Export and Local Markets, *Hassadeh*, 61(8):1284-1285 (1981).
Karchi et al., "The Importance of Cultural Practices in Materializing Yield Potential in a Tetraploid Watermelon Cultivar," *Cucurbit Genetics Cooperative Report CGC6-30*, 6(article 30):59-61 (1983).
Kemble, "Watermelon Grader's Guide ANR-681," *Alabama Cooperative Extension System*, pp. 1-4 (2001).
Kumar, Inheritance of Fruit Yield and other Horticulturally important Traits in Watermelon [*Citrullus lanatus* (Thunb.) Matsum. & Nakai]., Ph.D. Thesis, North Carolina State University, pp. 1-128 (2009).

(56) References Cited

OTHER PUBLICATIONS

Lam et al., "Grafted Seedless Watermelon Trial in Southwest Indiana (2006)," *Southwest Purdue Agricultural Program*, Purdue University, pp. 1-4 (2006).
Leskovar et al., "Deficit Irrigation Influences Yield and Lycopene Content of Diploid and Triploid Watennelon," *Acta Hort.*, 628:147-151 (2003).
Leskovar et al., "Lycopene, carbohydrates, ascorbic acid and yield components of diploid and triploid watermelon cultivars are affected by deficit irrigation," *Journal of Horticultural Science & Biotechnology*, 79(1):75-81 (2004).
Levi et al., "A Genetic Linkage Map for Watermelon Based on Randomly Amplified Polymorphic DNA Markers," *J. Amer. Soc. Hort. Sci.*, 126(6):730-737 (2001).
Levi et al., "An Extended Genetic Linkage Map for Watermelon Based on a Testcross and a $BC_2F_2$ Population," *American Journal of Plant Sciences*, 2:93-110 (2011).
Levi et al., "Genetic diversity among watermelon (*Citrullus lanatus* and *Citrullus colocynthis*) accessions," *Genetic Resources and Crop Evolution*, 48:559-566 (2001).
Levi et al., "Low Genetic Diversity Indicates the Need to Broaden the Genetic Base of Cultivated Watermelon," *HortScience*, 36(6):1096-1101 (2001).
Lou, "Inheritance of Fruit Characteristics in Watermelon [*Citrullus lanatus* (Thunb.) Matsum. & Nakai]," Ph.D. Thesis, North Carolina State University, pp. 1-134 (2009).
Mao et al., "Incidence of water-soaking and phospholipid catabolism in ripe watermelon (*Citrullus lanatus*) fruit: induction by ethylene and prophylactic effects of 1-methylcyclopropene," *Postharvest Biology and Technology*, 33:1-9 (2004).
Martyn et al., "Resistance to Races 0, 1, and 2 of Fusarium Wilt of Watermelon in *Citrullus* sp. PI-296341-FR," *HortScience*, 26(4):429-432 (1991).
Maynard et al., "Triploid Watermelon Cultigen Evaluation Spring 2003," Gulf Coast Research and Education Center, GCREC Research Report BRA-2003, pp. 1-5 (2003).
Mitchell et al., "Fruit Yield, Quality Parameters, and Powdery Mildew (*Sphaerothea fuliginea*) Susceptibility of Speciality Melon (*Cucumis melo* L.) Cultivars Grown in a Passively Ventilated Greenhouse," Cucurbitaceae 2006, pp. 483-491 (2006).
Morales et al., "Seeded Watermelon Cultivar Trials for Southwestern Indiana, 2000," Department of Horticulture, Purdue University, pp. 1-2 (2000).
Morales et al., "Seedless Watermelon Cultivar Trials for Southwestern Indiana, 2000," Department of Horticulture, Purdue University, pp. 1-2 (2000).
Nerson et al., "Harvesting Watermelons Before Ripening Impairs Their Quality," *Hassadeh*, 62:606-607 (1981).
Netzer et al., "PI 296341, a Source of Resistance in Watermelon to Race 2 of *Fusarium oxysporum* f. sp. *niveum*," *Plant Disease*, 73(6):518 (1989).
Nip et al., "Physical, Chemical and Organoleptic Attributes of 'Charleston Gray' Watermelons at Different Stages of Maturity," *Proc. Amer. Soc. Hort. Sci.*, 93:547-551 (1968).
North Carolina Watermelon Association Newsletter, Oct. 10, 2003—Fall Edition, pp. 1-5 (2003).
Orange Fleshed Seedless Watermelon Varieties, *US Seedless Press*, pp. 1-2, n.d., *Web*, Oct. 1, 2014 <http://www.usseedless.com/orange_varieties.htm>.
Perkins-Veazie et al., "Flesh quality and lycopene stability of fresh-cut watermelon," *Postharvest Biology and Technology*, 31:159-166 (2004).
Perkins-Veazie et al., "Shelf Life of Minimally Processed Watermelon," *HortScience*, 33(4):605 (1998).
Picha, "Storage temperature influences watermelon quality," *Louisiana Agriculture*, 31(2):4-5 (1998).
Plant Variety Protection Certificate No. 8500103 for 'Charlee,' issued Oct. 31, 1986 in the name of Florida Agricultural Experiment Station.
Plant Variety Protection Certificate No. 8600105 for 'Minilee,' issued Jan. 30, 1987 in the name of Florida Agricultural Experiment Station.
PlantFiles: Watermelon *Citrullus lanatus* 'Alena,' *Dave's Garden*, pp. 1-2, n.d., *Web*, Dec. 23, 2009 <http://davesgarden.com/guides/pf/go/92716/index.html>.
Porter, "Inheritance of Certain Fruit and Seed Characters in Watermelons," *Hilgardia*, 10(12):489-509 (1937).
Risse et al., "Sensitivity of Watermelons to Ethylene During Storage," *HortScience*, 17(6):946-948 (1982).
Risse et al., "Storage Characteristics of Small Watermelon Cultivars," *J. Amer. Soc. Hort. Sci.*, 115(3):440-443 (1990).
Saha et al., "Evaluation of Seedless Watermelon Varieties for Production in Southwest Indiana—2010," *Midwest Vegetable Trial Report for 2010*, pp. 1-7 (2010).
Saha et al., "Evaluation of Triploid Personal-size Watermelon Varieties for Production in Southwest Indiana—2010," *Midwest Vegetable Trial Report for 2010*, pp. 1-3 (2010).
Saha et al., "Kentucky Triploid Watermelon Variety Trial—2014," *Midwest Vegetable Trial Report for 2014*, pp. 1-6 (2014).
Saha et al., "Midwest Personal-Size Triploid Watermelon Variety Trial in Southwest Indiana—2011," *Midwest Vegetable Trial Report for 2011*, pp. 1-3 (2011).
Saha et al., "Midwest Triploid Watermelon Variety Trial in Southwest Indiana—2011," *Midwest Vegetable Trial Report for 2011*, pp. 1-4 (2011).
Saha et al., "Southwest Indiana Triploid Watermelon Variety Trial—2013," *Midwest Vegetable Trial Report for 2013*, pp. 1-10.
Saha et al., "Watermelon and Muskmelon Variety Trials 2010," *Midwest Vegetable Trial Report for 2010*, pp. 1-27 (2010).
Saha, "Evaluation of Diploid Watermelon Varieties for Production in Southwest Indiana—2010," *Midwest Vegetable Trial Report for 2010*, pp. 1-2 (2010).
Saha et al., "Southwest Indiana Triploid Watermelon Variety Trial—2012," *Midwest Vegetable Trial Report for 2012*, pp. 1-8 (2012).
Sandlin, "Genetic Mapping in *Citrullus lanataas*," Master of Science Thesis, University of Georgia, pp. 1-84 (2010).
Schultheis et al., "2006 Cucurbit Cultivar Evaluations," *Horticultural Research Series No. 165*, North Carolina State University, pp. 1-69 (2006).
Showalter, "Deformation and Breakage Properties of Watermelon Flesh," Watermelon Flesh Studies, *Proc. Fla. State Hort. Soc.*, 81:235-239 (1968).
Slater et al., "Plant Biotechnology: the genetic manipulation of plants 39," Chapter 2: Plant tissue culture, Chapter 2, *Oxford University Press*, Oxford, pp. 37-53 (2003).
Smith, "Embryo Culture of a Tomato Species Hybrid," *Proc. Am. Soc. Hort. Sci.*, 44:413-416 (1944).
Srivastava et al., Tissue culture and plant regeneration of watermelon (*Citrullus vulgaris* Schrad. cv. Melitopolski), *Plant Cells Reports*, 8:300-302 (1989).
Strang et al., "Triploid Mini-Watermelon Variety Trial," Department of Horticulture, University of Kentucky, pp. 1-4 (2004).
Toivonen et al., "Differences in Chlorophyll Loss at 13° C. for Two Broccoli (*Brassica oleracea* L.) Cultivars Associated with Antioxidant Enzyme Activities," *J. Agric. Food Chem.*, 46:20-24 (1998).
United States Standards for Grades of Watermelons, Effective Mar. 23, 2006, Fresh Products Branch, Fruit and Vegetable Programs, Agricultural Marketing Research, U.S. Department of Agriculture, pp. 1-10 (2004).
Watermelon Millionaire Seedless F1, *Harris Seeds*, pp. 1-2, n.d., *Web*, Jul. 11, 2015 <https://www.harrisseeds.com/storefront/p-406-watermelon-millionaire-seedless-fl.aspx>.
Wehner et al., "Breeding and Seed Production," In: D.N. Maynard (ed.), Watermelons: Characteristics, production, and marketing, *ASHS Horticulture Crop Production Series*, Chapter 3, pp. 27-73 (2001).
Wehner et al., "Qualitative Genes for Use in Development of Elite Watermelon Cultivars," *Cucurbit Genetics Cooperative Report*, 27:24-24 (2004).
Wehner et al., "Vegetable Cultivar Descriptions for North America List 27 2013," Vegetable Cultivar List, *HortScience*, 48(2):245, 276-286 (2013).

(56) References Cited

OTHER PUBLICATIONS

Wehner, "Watermelon," Department of Horticultural Science, North Carolina State University, Index of Cucurbit Wehner Articles, Book 16, pp. 368-405 (2007) <http://cuke.hort.nesu.edu/cucurbit/wehner/articles/book16.pdf>.
Yamasaki et al., "Mineral Concentrations and Cytokinin Activity in the Xylem Exudate of Grafted Watermelons as Affected by Rootstocks and Crop Load," *J. Japan. Soc. Hort. Sci.*, 62(4):817-826 (1994).
Yoo et al., "Variation of Carotenoid, Sugar, and Ascorbic Acid Concentrations in Watermelon Genotypes and Genetic Analysis," *Hort. Environ. Biotechnol.*, 53(6):552-560 (2012).
Zhumei et al., "Selection and cultivation of the high quality early ripe variety Nongfong No. 1 B," Pingzhong Shuanyu (*Chinese J. Selection and Cultivation of variety*), 3:11-13 (2004).
Declaration under 37 C.F.R. § 1.132 by Greg Tolla filed Jun. 27, 2012, U.S. Appl. No. 10/972,190.
Declaration under 37 C.F.R. § 1.132 by Greg Tolla filed Apr. 4, 2014, in U.S. Appl. No. 10/972,190.
Declaration under 37 C.F.R. § 1.132 by Greg Tolla filed Jan. 9, 2013, in U.S. Appl. No. 12/856,286.
Declaration under 37 C.F.R. § 1.132 by Greg Tolla filed Aug. 24, 2015, in U.S. Appl. No. 12/856,286.
Supplemental Response to Final Office Action filed Jun. 8, 2015, in U.S. Appl. No. 10/972,190.
Amendment and Response to Final Office Action filed May 28, 2015, in U.S. Appl. No. 10/972,190.
Amendment and Response to Non-Final Office Action filed Oct. 16, 2014, in U.S. Appl. No. 10/972,190.
Amendment and Response to Non-Final Office Action filed Apr. 4, 2014, in U.S. Appl. No. 10/972,190.
Amendment and Response to Final Office Action filed Jun. 27, 2012, in U.S. Appl. No. 10/972,190.
Amendment and Response to Non-Final Office Action filed Dec. 8, 2011, in U.S. Appl. No. 10/972,190.
Supplemental Response to Final Office Action filed Aug. 12, 2010, in U.S. Appl. No. 10/972,190.
Amendment and Response to Final Office Action filed January 8, 2010, in U.S. Patent Application No. 10/972,190
Amendment and Response to Non-Final Office Action filed Apr. 3, 2009, in U.S. Appl. No. 10/972,190.
Amendment and Response to Final Office Action filed Feb. 20, 2008, in U.S. Appl. No. 10/972,190.
Amendment and Response to Non-Final Office Action filed Jun. 20, 2007, in U.S. Appl. No. 10/972,190.
Amendment and Response to Restriction Requirement filed Nov. 13, 2006, in U.S. Appl. No. 10/972,190.
Amendment and Response to Final Office Action filed Jun. 1, 2016, in U.S. Appl. No. 12/856,286.
Amendment and Response to Non-Final Office Action filed Aug. 21, 2015, in U.S. Appl. No. 12/856,286.
Amendment and Response to Examiner's Answer and Request to Reopen Prosecution filed Dec. 18, 2014, in U.S. Appl. No. 12/856,286.
Appeal Brief dated May 9, 2014, in U.S. Appl. No. 12/856,286.
Amendment and Response to Final Office Action filed Jul. 26, 2013, in U.S. Appl. No. 12/856,286.
Amendment and Response to Non-Final Office Action filed Jan. 9, 2013, in U.S. Appl. No. 12/856,286.

\* cited by examiner

WATERMELON WITH IMPROVED PROCESSING QUALITIES

CROSS REFERENCE TO RELATED APPLICATIONS

This application is a continuation of U.S. application Ser. No. 12/856,286, filed Aug. 13, 2010 (now U.S. Pat. No. 9,420,753 issued Aug. 23, 2016), which is a continuation of U.S. application Ser. No. 10/972,190, filed Oct. 22, 2004 (now U.S. Pat. No. 9,173,356 issued Nov. 3, 2015), which claims the benefit of provisional Application No. 60/584,964, filed on Jul. 2, 2004, all of which are incorporated herein by reference in their entireties.

BACKGROUND OF THE INVENTION

Field of the Invention

The field of the present invention is watermelon breeding and the genetic improvement of watermelon. More specifically, this application is related to diploid, tetraploid and triploid watermelon seeds and plants for the production of watermelon fruit that (i) have ultra firm flesh and/or liquid-retaining flesh and (ii) are sweet at maturity.

Description of Related Art

Watermelon (*Citrullus lanatus*) is an important commercial member of the Cucurbitaceae family that includes many different varieties. The fruit of these varieties differ in coloring, sweetness, and other traits. For example, watermelon fruit of different varieties display a wide range of coloring on the outside rind. In addition, color in the edible tissue varies from different shades of red to yellow. Watermelon fruit also vary in sweetness, which can be estimated by measuring total soluble solids, or brix, using a refractometer. Because sweetness is especially important to consumers, the U.S. Department of Agriculture has set fruit quality standards based on brix levels (United States Standards for Grades of Watermelon, U. S. Department of Agriculture (1978)). According to these standards, edible parts of the fruit having not less than 8 brix are deemed to be "Good", while edible parts of the fruit having not less than 10 brix are deemed to be "Very Good."

Consumers also have the choice of either seeded or seedless watermelon varieties. Unlike the flesh coloring, which is caused by varying genetic loci, the distinction between seeded and seedless varieties is usually caused by human intervention of making crosses that vary ploidy levels. Similar to humans, watermelons are natural diploids with chromosomes arranged in pairs. Many plants, including watermelons, can undergo a duplication of their entire set of chromosomes and exist as tetraploids. While it is uncommon for watermelons to produce spontaneous tetraploids, this process can be routinely produced in the laboratory using cell biology techniques. A tetraploid parent may then be crossed with a diploid parent to produce triploid seeds, which, in turn, generate plants with seedless fruits. In particular, seed formation in the fruit of triploid plants aborts because of the ploidy level differences, resulting in seedless fruits. Many commercial varieties are triploid and seedless.

Fruits of plants of different ploidy also vary in flesh firmness. Diploid lines typically have the lowest fruit flesh firmness levels. For reasons that are unclear, the process of changing a diploid line to a tetraploid line correlates with firmer fruit flesh. In other words, tetraploid lines usually have firmer fruit flesh than diploids. Triploids, being a cross between a tetraploid and a diploid, typically have an intermediate level of flesh firmness.

In addition to consumer preferences as to coloring, sweetness and seeds, there is increasing consumer demand in the fresh produce business for products that combine quality and convenience. Examples of products that meet these criteria are bagged baby carrots, broccoli and cauliflower and bagged leafy crops, such as lettuce and spinach. Similarly, there is demand for mature cut fruits, like watermelon, melon, pineapple, *papaya* and kiwi. A growing segment of watermelon retail sales are cut fruits that are either displayed in large pieces with the rinds attached, or are cut into smaller pieces, without the rind, and offered to the consumers in plastic food containers. The industry term for these products is "minimally processed." By 1998, Perkins-Veazie et al. ((1998) Hortscience 33:605) estimated that 10% of the retail watermelon market was minimally processed.

The advantage of such cut fruit displays is that the consumer can visually inspect the quality of the fruit and, in particular, judge whether the fruit is mature and, thus, ready to consume. Often, immature fruits will not be uniform in pigmentation, and overripe fruit will display signs of decay. Moreover, these products offer convenience to the consumer.

The disadvantage to the produce retailer in presenting minimally processed watermelon products is that cut fruits have a short shelf life. Studies indicate that minimally processed products have a shelf life of 2 to 3 days maximum (ibidem; Wehner et al. In: Watermelons: Characteristics, Production and Marketing. Maynard, editor. ASHS Press, Alexandria, Va. (2001).)

Watermelon fruits currently available typically undergo rapid quality deterioration after being cut. Cutting the fruit causes decay, which is observed as a softening of the fruit texture. Deterioration is also manifested as liquid leakage; in some varieties, the flesh of a fresh cut watermelon fruit quickly becomes unattractive to the consumer. The rapid deterioration of cut watermelon fruit places both time and space constraints on the retailer. Because cut fruits have a short shelf life, the retailer typically performs the processing on the retail site. In addition, the retailer has to monitor the products often to ensure that deteriorating products are discarded.

Unlike the sweetness standards established by the U.S. Department of Agriculture, there are no industry standards to describe the firmness of the edible portions of watermelon fruits. Therefore, there are a wide range of descriptors in use, from "firm" and "crisp" (Erma Zaden catalog descriptors for varieties Gil 104 and Erma 12) to "very firm flesh" (Zhang et al. in USPTO application numbers 20040060085 and 20030217394 and Seminis watermelon catalog for the variety Cooperstown). Seminis has described cultivars Fenway, Royal Star and Sentinel as having "excellent crispness," "firm flesh" and "crisp juicy flesh," respectively. In addition, Rogers Seed Company advertises the Tri-X Brand 626 as "exceptionally firm" and the Tri-X Brand 313 as having "firm texture" and "crispness."

While advertising terminology used to describe watermelon fruit flesh firmness is quite variable, scientific reports, using quantitative measurements, show that typical commercial germplasm have had substantially lower flesh firmness than the watermelon fruit of this invention. For example, Roberts et al. (2004 Report from: Watermelon Research and Development Working Group. 24th Annual Meeting, Tulsa, Okla.) measured flesh firmness in a wide range of germplasm, using a penetrometer to measure the amount of force resisted. The data were reported in Newtons, an International System of Measurements term. For purposes of comparison with Applicants' penetrometer measurements, Applicants converted Roberts' data to pounds force (lbf), using the following formula: 1 lbf=4.448 Newtons. Roberts reports a range of watermelon flesh firmness between approximately 6.227 to 15.123 Newtons (1.4 to 3.4 lbf). One of the lines analyzed is Rogers Seed Company line Tri-X Brand 313. As noted above, Rogers Seed Company advertises this line as having "firm" flesh. Roberts et al. measured the flesh firmness in Tri-X Brand 313 as 10.84 Newtons, which converts to approximately 2.4 lbf. Applicants also tested the flesh firmness of Tri-X Brand 313, using a penetrometer from QA Supplies in Norfolk, Va. (Model FT011) with a probe diameter of 8 mm. Using this methodology, Tri-X Brand 313 has a flesh firmness reading of 6.227 Newtons (1.4 lbf) (Table 1). Because Roberts does not report the size of the penetrometer probe used, Applicants cannot directly compare their data to Roberts'. At least for Tri-X Brand 313, the approximately 77% higher reading measured by Roberts et al. compared with the protocol described herein may be the result of different methodology, and, in particular, the use of differently sized penetrometer probes. Although the Applicants of this invention use an 8 mm probe, another commonly used penetrometer has a diameter of 11 mm, which would account for the different readings, as penetrometer area is approximately 73% higher for an 11 mm probe as compared to an 8 mm probe.

Schultheis and Thompson (2004 Report from: Watermelon Research and Development Working Group. 24$^{th}$ Annual Meeting, Tulsa, Okla.) also survey watermelon fruit flesh firmness. Although these authors use a different model penetrometer than that used by Applicants, they use a very similarly sized probe with a diameter of 5/16" or about 8 mm. Schultheis and Thompson report that line Tri-X 313 had flesh firmness readings between 1.4 and 1.7, which are similar to Applicants' measurements, shown in Table 1. In this report, however, the authors describe these firmness data in units of pounds/square inch. It is suspected, however, that the units provided in the Schultheis and Thompson report should be in pounds force, as a reading of 1.4 pounds/square inch, using a 5/16" probe, is only 0.667 Newtons (0.15 pounds force).

Maynard and Sidoti (2003 GCREC Research Report BRA-2003; Univ. Florida, Gulf Coast Research and Education Center, Bradenton, Fla.) report an additional survey of fruit flesh firmness of commercial watermelon lines. In this study, the authors use a different model penetrometer than that Applicants use in the method described herein, with a larger sized probe having a diameter of 7/16" or about 11 mm. Their firmness data range from 1.8 to 3.0 pounds/square inch. As with the Schultheis and Thompson report, Applicants believe that these authors are using the incorrect units in their firmness readings. Assuming that these data are actually in pound force units, they compare well with the results obtained using the methodology described herein. For example, Maynard and Sidoti's firmness measurement of line Tri-X 313 was 2.6. If one adjusts this figure to correct for the approximate 2 times difference in probe area, the new figure is 1.35, which is nearly identical to Applicants' measurement of this same line, (Table 1). On the other hand, if one assumes that the data are correctly reported in lb/square inch, the figure of 2.6 lb/square inch based on a 7/16" probe would be reading of 1.735 Newtons (0.39 lbf). The Tri-X 313 line should have a much higher firmness reading than 1.735 Newtons (0.39 lbf), providing further evidence of inconsistency in how such units have been reported in the prior art.

Leskovar et al. ((2004) J. Horticultural Science and Biotechnology 79: 75-81) also report watermelon fruit firmness. Although this manuscript uses a different measurement protocol, the authors describe in detail their methods, allowing the data to be converted for comparison with the data described herein. After converting to the same units, the range of germplasm analyzed had fruit firmness between 4.003 Newtons (0.9 lbf) and 6.672 Newtons (1.5 lbf).

Although measurements of the prior art can be confusing, there is clarity that commercial watermelon lines produced prior to this invention have fruit firmness that is well below 13.344 Newtons (3 lbf). In addition, as shown in Example 4, the fruit of such commercial watermelon lines, once cut, undergo significant liquid leakage. The present invention, therefore, addresses the need in the marketplace for watermelon lines that produce fruits that have a longer shelf life when processed. Specifically, the watermelon of this invention have (i) ultra firm flesh, which avoids the problem of cut fruit becoming overly soft, and/or (ii) liquid-retaining flesh, which delays deterioration of cut fruit by liquid leakage. In addition, these fruits have quality characteristics desired by the consumer, such as sweetness and attractiveness, and offer the retailer both flexibility as to where fruit processing occurs and additional shelf life once fruit is processed.

SUMMARY OF THE INVENTION

This invention relates to unique watermelon inbred lines and hybrid varieties that produce fruit having ultra firm edible flesh at maturity that resists at least 13.344 Newtons (3.0 Pounds force (lbf)) (measurement techniques defined herein). In addition to the novel ultra firm flesh phenotype, these fruits meet market requirements for sweetness, having not less than 6 brix for the edible tissue (measurement techniques defined herein).

Watermelons of this invention are preferably diploid and tetraploid inbred lines that produce sweet tasting ultra firm flesh at maturity that resists at least 15.568 Newtons (3.5 lbf), though lines that produce sweet tasting ultra firm flesh at maturity that resists at least 17.792 Newtons (4 lbf), 22.240 Newtons (5 lbf), 26.688 Newtons (6 lbf) and even 35.584 Newtons (8 lbf) are also contemplated by this invention. A plurality of watermelon plants grown in a field are also provided by the invention.

Any diploid or tetraploid inbred line having ultra firm flesh created from the teachings of this invention can transmit this ultra firm flesh phenotype to a hybrid. In addition to having ultra firm flesh at maturity, the watermelons of the present invention are capable of developing uniformly pigmented fruit flesh (red, yellow, or orange). In addition, at maturity, fruits from these inbred lines and hybrids will meet or exceed industry standards for sweetness, being at least good (not less than about 8 brix) and preferably very good (not less than about 10 brix).

The invention also provides a method for producing hybrid watermelon seed comprising crossing an inbred watermelon plant with a second watermelon plant and harvesting resultant hybrid watermelon seed, as well as a hybrid watermelon plant produced by growing the resultant hybrid watermelon seed.

The invention further provides a method for producing the ultra firm watermelon plant comprising the steps of crossing a watermelon variety having a level of sweetness that at least meets industry standards with a low sweetness watermelon variety having ultra firm flesh; performing at least one backcross with the variety having a level of sweetness that at least meet industry standards, and performing one or more cycles of self-pollination of products of the backcross (or recurrent backcross) having the combined traits of ultra firm flesh and sweetness that at least meets industry standards. The method may utilize as a watermelon having ultra firm flesh the watermelon plant of USDA Collection No. PI296341.

Watermelon fruit and watermelon flesh derived from the ultra-firm watermelon are also contemplated. Preferred are watermelon plants producing a fruit weighing at least about 1.5 kg, more preferably producing a fruit weighing at least about 3.0 kg. In a further preferred embodiment the watermelon plant produces a fruit weighing at least about 4.5 kg, and in a still further preferred embodiment the plant produces a fruit weighing at least about 6.0 kg.

The invention also provides a watermelon plant having the soluble solids and flesh firmness traits of a plant produced from seed deposited as Accession No. NCIMB 41230, made on Jul. 1, 2004, as well as seed, pollen, ovule and other vegetative tissue derived from the plant, or a watermelon plant regenerated from such tissue.

The invention also provides a watermelon plant with liquid-retaining flesh. As explained in detail below, this liquid-retaining trait corresponds to the amount of weight that cut watermelon fruit flesh loses over time. Preferred are watermelon plants wherein cut flesh from the watermelon fruit loses less than about three and one-half percent of its weight after three days storage at 4° centigrade. More preferred are such watermelon plants where the cut flesh loses less than about three percent weight after three days storage at 4° centigrade. A still further preferred watermelon plant is provided where the cut flesh loses less than about two percent weight after three days storage at 4° centigrade. In another preferred embodiment, the watermelon plant has cut flesh that loses less than about one and one-half percent weight after three days storage at 4° centigrade. This liquid-retaining trait extends the shelf life of processed watermelon fruit.

A preferred embodiment is a good ultra firm flesh watermelon diploid inbred line that produces sweet tasting mature fruit. Another preferred embodiment is a triploid hybrid, created using as at least one parental line that is either an ultra firm flesh diploid inbred line or an ultra firm flesh tetraploid inbred line that produces good standard sweet tasting mature fruit with ultra firm flesh. In another preferred embodiment the mature watermelon fruit produced in the diploid, tetraploid, or triploid plants of this invention develop full red flesh color and are sweet tasting, with good brix levels.

In yet another preferred embodiment, mature watermelon fruits of this invention develop full yellow flesh color and good sweetness in combination with ultra firm flesh. In still yet another preferred embodiment, the mature watermelon fruits of this invention develop full orange color and good sweetness in combination with ultra firm flesh. In another preferred embodiment the watermelon flesh from fruits of this invention stays ultra firm after being minimally processed (fresh cut fruit). This ultra firm feature extends the shelf life of the processed fruit.

The present invention also relates to a novel method of producing diploid and tetraploid watermelon lines and triploid watermelon hybrids that produce sweet tasting mature fruit with ultra firm flesh (resists pressure of at least 17.792 Newtons (4.0 lbf); not less than 8 brix).

One step in this method involves crossing a known watermelon variety or line with a watermelon line of this invention having ultra firm flesh at maturity. The product of such cross is then self-pollinated to create a segregating population. In successive generations, individuals from populations segregating for the ultra firm flesh trait are subjected to successive cycles of selection and breeding and the end result is a new watermelon line that produces sweet tasting mature fruit having ultra firm flesh.

Other objects, features and advantages of this invention will become apparent from the detailed description that follows. It should be understood that the detailed description and examples, while stating preferred embodiments of the invention, are by way of illustration only, as modifications and changes within the scope of the invention will become apparent to those skilled in the art.

DETAILED DESCRIPTION OF THE INVENTION

Figure 1:
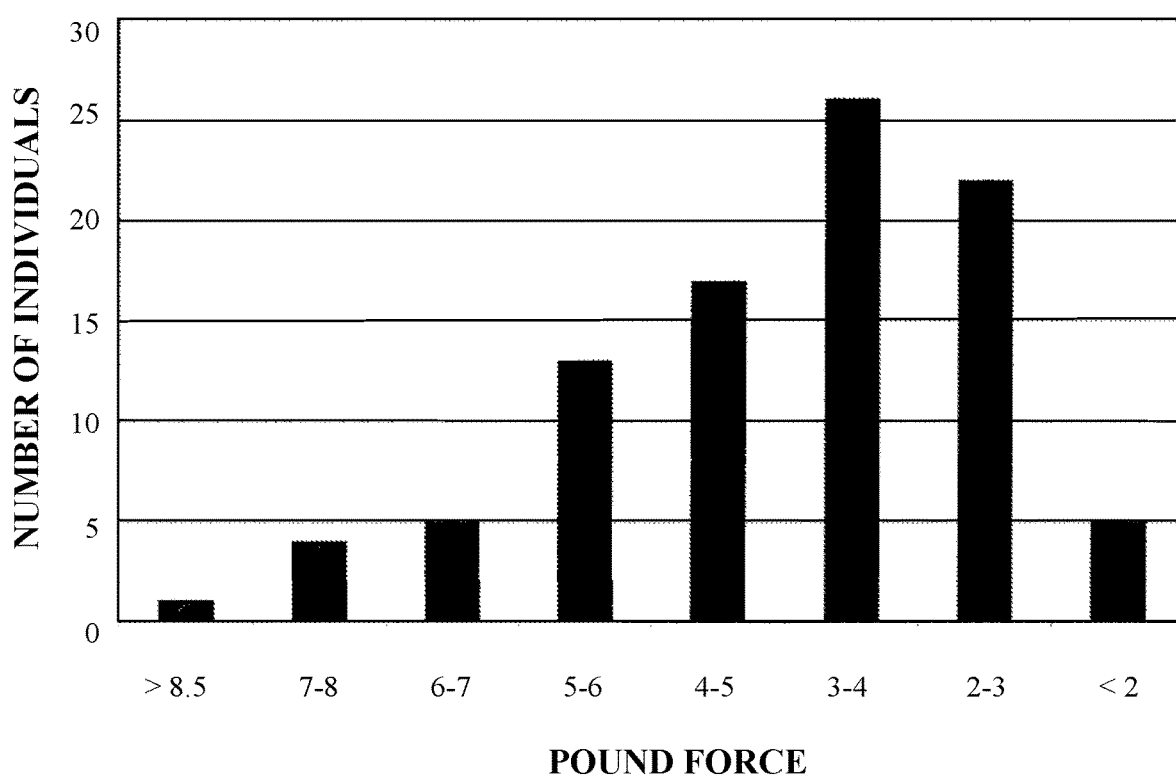
FIG. 1 is a histogram that illustrates fruit flesh firmness of the third generation of self-pollinated inbred watermelon plants of the present invention. The arrow indicates the average mature fruit firmness of the recurrent parent lines. The shaded portion of the histogram shows that 43% of these fruits have firmness readings at or above 17.792 Newtons (4 lbf).

The present invention provides a watermelon plant that produces fruit with (i) ultra firm flesh and/or liquid-retaining flesh and (ii) sweetness of at least 6 brix. Therefore, the fruit of this invention have improved processing qualities, as, once cut, the fruit remains firm and/or retains its juice considerably longer than the commercial watermelon lines of the prior art.

Definitions

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seed, leaves, stems and the like.

As used herein, "diploid plants" means plants or transplants derived from planting diploid seeds or from micropropagation that have two sets of chromosomes in the somatic cells, or twice the haploid number.

"Triploid plants" refers to plants or transplants derived from planting triploid seeds or from micropropagation that have three sets of chromosomes in the somatic cells, or three times the haploid number.

"Tetraploid plants" are plants or transplants derived from planting tetraploid seeds or from micropropagation that have four sets of chromosomes in the somatic cells, or four times the haploid number.

The term "firm flesh" refers to the edible flesh of a watermelon for which fruit firmness, as measured using a penetrometer by the methods described in Example 2, is greater than about 6.672 Newtons (1.5 lbf) of pressure but less than or equal to about 8.896 Newtons (2.0 lbf). Botanically, the edible flesh of a watermelon fruit is placental tissue.

The descriptor "ultra firm flesh" refers to the edible flesh of a watermelon with fruit firmness, as measured using a penetrometer by the methods described in Example 2, measuring not less than 13.344 Newtons (3.0 lbf) of pressure, or with higher firmness than fruit produced by standard known cultivars. Ultra-firm flesh watermelon preferably has fruit firmness of about 15.568 Newtons (3.5 lbf).

The term "very firm flesh" refers to the edible flesh of a watermelon with firmness, as measured using a penetrometer by the methods described in Example 2, greater than about 8.896 Newtons (2.0 pound force) of pressure but less than 13.344 Newtons (3.0 lbf).

The term "liquid-retaining flesh" refers to edible flesh of a watermelon which, once cut, loses less than about four percent of its weight after three days storage at 4° centigrade, or retains more liquid, over time, than fruit produced by standard known cultivars. About 95-98% of the weight lost from cut watermelon fruit is estimated to be due to liquid leakage. The majority of the remaining weight loss is from soluble solids, such as sugars and acids. Therefore, liquid loss may be approximated by measuring the percent weight loss of watermelon fruit, once cut, over time.

A "penetrometer" is a device designed to measure force and is used herein to measure fruit firmness. It provides a quick, easy and accurate method to determine fruit flesh and skin firmness. Applicants gathered the data reported herein using a hand-held penetrometer to obtain three to five pressure readings on mature fruit. Specifically, Applicants used Penetrometer model FT011 (QA Supplies, Norfolk, Va.) with an 8 millimeter, or approximately 5/16 inch, probe.

"Pounds force", or "lbf", is the unit read by the penetrometer model FT011, and is used herein exclusively to indicate readings made using the 8 millimeter probe, unless otherwise indicated.

Coloration of the rind in watermelons, also referred to as "rind pattern", can vary from light green, often termed gray, to medium green, to very dark green, appearing to be almost black. In addition, the rind may have stripes of various designs which are typical of a variety or type. Therefore, the terms "tiger stripe", "mottle stripe", "dark mottle stripe", and the like, are used to identify various patterns.

As used herein, "length to width ratio (L/W ratio)" means the ratios obtained in any of the possible combinations by taking the average length divided by the average width on the watermelon fruit. The ratios can vary from 1:1.2 to 2.2:1.

The term "population" refers to genetically heterogeneous collection of plants sharing a common parental derivation.

As used herein, the term "variety" or "cultivar" refers to a group of similar plants that, by their genetic pedigrees and performance, can be identified from other varieties within the same species.

"Backcrossing" refers to the process in which a breeder crosses a plant with one of its parent lines.

"Recurrent backcrossing" is a breeding strategy designed to recover the genetic composition of a line by crossing a plant in succession back to one of the parent lines.

The term "soluble solids" refers to the percent of solid material found in edible fruit. As used herein, soluble solids are measured quantitatively with a refractometer as percentage brix. Refractometers often include a sucrose scale, as brix is formally defined as weight percent sucrose. If the only soluble solid present in an aqueous solution is sucrose, the sucrose scale should give the actual percentage sucrose. However, if other soluble solids are present, as is almost always the case, the reading is not equal to the percentage sucrose, but approximates the overall percentage soluble solids in the sample. In short, although brix is technically defined as weight percent sucrose, those of skill in the art recognize that weight percent soluble solids, as obtained with a refractometer, approximates weight percent sucrose and accurately indicates sweetness. Therefore, the higher the percentage soluble solids, as indicated by brix level, the higher the perceived sweetness of the fruit.

The U.S. Department of Agriculture has established watermelon fruit quality standards based on brix levels (United States Standards for Grades of Watermelon, U. S. Department of Agriculture (1978)). According to these standards and as used herein, edible parts of the fruit having not less than 8 brix are referred to as "good", while edible parts of the fruit having not less than 10 brix are referred to as "very good."

"Sweetness", as used herein, may be measured quantitatively, as described above, using a refractometer, or qualitatively, by taste.

A "quantitative trait loci", or "QTL" is a chromosomal location that encodes for alleles that affect the expressivity of a continuously distributed phenotype.

"Maturity" refers to maturity of fruit development and indicates the optimal time for harvest. Generally, growers of skill in the art harvest fruit at or substantially near its maximum sweetness and flavor intensity. In watermelon, the maturity comes associated with changes in rind appearance, flesh color and sugar content.

The terms "homozygous" and "homozygosity" are genetic terms. When identical alleles reside at corresponding loci on homologous chromosomes, that locus is called homozygous. Homozygosity typically refers to the degree to which a population is fixed at one or more loci.

A "hybrid" is an offspring of a cross between two genetically unlike individuals.

An "inbred" or "inbred line" is a substantially homozygous individual or variety.

"Introgress" is the process a breeder performs to introduce a new trait, usually from a non-cultivated type, into a cultivated type.

Typical Characteristics of Commercial Watermelon Fruit

Successful watermelon production depends on attention to various cultural practices. These include soil management, with special attention to proper fertilization; crop establishment, with appropriate spacing; weed control; the introduction of bees for pollination and, if producing fruit from triploid plants, a suitable pollen source for producing seedless (triploid) watermelon; irrigation; and pest management. Watermelon fruit size and shape, rind color, thickness and toughness, seed size, color and number, flesh color, texture, sugar content and freedom from fruit defects are all important characteristics to be considered in selection of watermelon varieties. Commercial seed companies typically offer the grower an opportunity to observe these characteristics in demonstration plots of their varieties, and some agricultural universities perform cultivar analysis data for the local growers (Roberts et al. (2004), Maynard and Sidoti (2003), Schultheis and Thompson (2004) and Leskovar et al. (2004)).

Watermelon crops can be established from seed or from transplants. Transplanting is becoming more common because transplanting can result in an earlier crop compared with a crop produced from direct seeding. When a grower wants to raise a seedless fruited crop, transplanting is preferred. Transplanting helps achieve complete plant stands rapidly, especially where higher seed costs, as with triploid seeds, make direct-seeding risky.

Watermelon is the only economically important cucurbit with pinnatifid (lobed) leaves; all of the other species have whole (nonlobed) leaves. Watermelon growth habit is a trailing vine. The stems are thin, hairy, angular, grooved, and have branched tendrils at each node. The stems are highly branched and up to 30 feet long (Wehner et al. In: Watermelons: Characteristics, Production and Marketing. Maynard, editor. ASHS Press, Alexandria Va. 2001).

Watermelon breeders are challenged with anticipating changes in growing conditions, new pathogen pressure, and changing consumer preferences. With these projections, a breeder will attempt to create new cultivars that will fit the developing needs of growers, shippers, retailers, and consumers. Thus the breeder is challenged to combine in a single genotype as many favorable attributes as possible for good growing, distribution, and eating. One important characteristic for the breeder is fruit size. Fruit size is an important consideration because there are different market requirements for particular groups of shippers and consumers. The general categories are: icebox (<12 lb), small (12-18 lb), medium (18-24 lb), large (24-32 lb), and giant (>32 lb). Fruit size is inherited in polygenic fashion, with an estimated 25 genes involved. Fruit is distributed from the grower to the retailer by shippers, who focus on particular weight categories, such as 18-24 lb for seeded and 14-18 lb for seedless. Although historic consumption has been for these general categories of sizes, there is an increasing trend in the marketplace for a new class of small-fruited watermelon hybrids (with fruit weight between 3-9 lb).

Fruit flesh firmness and liquid retention are other important characteristics. Consumers have varying textural preferences for watermelon fruit, and flesh firmness is a determinant of texture. Additionally, flesh firmness is a critical parameter that determines how long cut fruit will last on the retailer's shelf. Liquid retention is also critical to consumer perception of minimally processed watermelon. Cut fruit shelf life research is usually qualitative, with evaluations on when the fruits become 'slimy' (Perkins-Veazie et al. 1998 HortScience 33: 605). Quantitative evaluations of cut fruit shelf life include measuring the flesh firmness directly, using a penetrometer, or measuring percent weight loss of cut fruit over time in order to approximate liquid leakage, as described in Example 4.

Applicants were also able to determine the firmness of various fruit simply by eating them. Indeed, this was how applicants first determined that the watermelons of this invention have ultra firm flesh compared to prior art watermelons. In taste tests, Applicants also determined that standard cultivars of the prior art, such as Seminis' diploid Royal Star line, have firm flesh, while the following lines have firm to very firm flesh: Tri-X Brand 626 (Syngenta/Rogers—triploid), Extazy (Hazera—triploid) and Solitaire (Golden Valley—triploid).

Another important fruit characteristic is quality, which includes sweetness and attractiveness of fruit and rind color. Wehner et al. (in: Watermelons: Characteristics, production and marketing. Maynard, editor. ASHS Press. Alexandria, Va. (2001)) describe these characteristics. Among the most important of these characteristics is sweetness, without a bitter taste, which is measured by brix and by taste. Taste panel data demonstrated a direct correlation of good flavor scores with higher brix levels (Nip et al. (1968) Proc. Amer. Soc. Hort. Sci. 93:547). Brix levels increase as the fruit develops and ripens on the vine. Thus, immature fruits will have unacceptably low sweetness to the consumer; if picked too early, the edible tissue will also not have uniform color. Quantitative recommendations for watermelon fruits have been published. While Wehner et al. suggest brix levels between 10% and 14% brix, the U.S. Department of Agriculture has established standards, as described in detail in the "Definitions" section, in which sweetness of at least 8 brix is good and sweetness of at least 10 brix is very good. Despite some variation in the recommendation and the standards, there is no dispute that fruit sweetness is a critical characteristic of watermelon fruit.

Characteristics of Watermelon Fruit of the Present Invention

Fruit Firmness

The flesh of watermelon plant fruits of the present invention is firmer and retains liquid better than the fruit flesh of watermelon cultivars of the prior art. In prior art watermelon fruit, mature edible flesh from diploid genotypes are softer than both triploid and tetraploid genotypes. Fruit firmness variation within a line, irrespective of ploidy level, is insignificant. In general, standard diploid cultivars produce fruits with soft to at best firm flesh (i.e., flesh firmness at maturity from less than 4.448 Newtons (1.0 lbf) to about 6.672 Newtons (1.5 lbf)). Standard tetraploid lines typically produce fruit with firm flesh or very firm flesh (i.e., flesh firmness between 6.672 Newtons (1.5 lbf) to less than about 13.344 Newtons (3.0 lbf) at maturity). Standard triploid hybrids produce seedless fruit with an intermediate level of flesh firmness at maturity, ranging from about 5.782 Newtons (1.3 lbf) to 11.120 Newtons (2.5 lbf). Table 1 shows flesh firmness data from the prior art for commercial hybrids and inbred watermelon lines.

All firmness measurements herein were made using a model FT011 penetrometer from QA Supplies in Norfolk, Va. with an 8 millimeter probe diameter. Readings were made and are reported in pounds force, a British Engineering measurement for pressure, which is abbreviated lbf and is converted to Newtons according to the following formula: 1 lbf=4.448 Newtons. Subject fruits were cut equatorially, midway between the blossom and stem ends of each fruit. Applicants made three to five readings per fruit, taking samples from the center of each cut fruit. Reported firmness data is an average of these three to five readings.

TABLE 1

Survey of firmness in typical watermelon cultivars and inbred lines. Average firmness readings are in pound force by methodology described herein.

| Line | Origin | Ploidy | Firmness (Newtons (lbf)) |
|---|---|---|---|
| Tri-X 313 | Syngenta/Rogers | Triploid | 6.227 (1.4) |
| Millionaire | Harris Moran | Triploid | 8.006 (1.8) |
| Revolution | SunSeeds | Triploid | 7.562 (1.7) |
| Majestic | Seminis | Triploid | 7.562 (1.7) |
| Olympia | Seminis | Triploid | 7.117 (1.6) |
| Omega | Seminis | Triploid | 6.672 (1.5) |
| PS110-5288-9 | Seminis | Triploid | 10.230 (2.3) |
| 4082 | Seminis | Tetraploid | 8.896 (2.0) |
| 4084 | Seminis | Tetraploid | 6.672 (1.5) |
| 4090 | Seminis | Tetraploid | 7.117 (1.6) |
| 4133 | Seminis | Tetraploid | 9.786 (2.2) |
| 4134 | Seminis | Tetraploid | 10.675 (2.4) |
| 4135 | Seminis | Tetraploid | 9.786 (2.2) |
| 4137 | Seminis | Tetraploid | 12.010 (2.7) |
| 4138 | Seminis | Tetraploid | 9.786 (2.2) |
| 47602A | Seminis | Diploid | 6.672 (1.5) |
| 4203 | Seminis | Diploid | 6.227 (1.4) |
| Cooperstown | Seminis | Triploid | 6.672 (1.5) |
| Fenway | Seminis | Triploid | 9.341 (2.1) |
| Sentinel | Seminis | Diploid | 6.227 (1.4) |
| W-1128 | Seminis | Diploid | 6.227 (1.4) |

TABLE 1-continued

Survey of firmness in typical watermelon cultivars and inbred lines.
Average firmness readings are in pound force by methodology
described herein.

| Line | Origin | Ploidy | Firmness (Newtons (lbf)) |
| --- | --- | --- | --- |
| W-1119 | Seminis | Diploid | 7.117 (1.6) |
| BSI 2532 | Seminis | Diploid | 7.562 (1.7) |
| BSI 2527 | Seminis | Diploid | 5.782 (1.3) |
| W-2068 | Seminis | Diploid | 4.893 (1.1) |
| W-2741 | Seminis | Diploid | 5.782 (1.3) |
| W-1488 | Seminis | Diploid | 7.562 (1.7) |
| BSI 2543 | Seminis | Diploid | 5.338 (1.2) |

Compared to prior art watermelon lines, the fruit of the present invention both have ultra firm flesh and are sweet. Table 2 displays flesh firmness and sugar content from watermelon line PI296341, which was used as the source of the novel firm flesh fruit of this invention, and hybrid lines created according to the methods described herein. Sweetness measurements were determined quantitatively, using a refractometer (Leica Microsystems Model AR200, Reichert Inc., Depew, N.Y.), according to manufacturer's instructions. One measurement was taken from each half of an equatorially cut fruit. The data were recorded as an average.

As indicated by comparing the firmness readings in Table 2 to those in Table 1, the flesh of the watermelon fruit of the present invention is considerably more firm than the flesh of the watermelon fruit of the prior art. Specifically, watermelon fruit of the present invention resist pressure of at least about 13.344 Newtons (3.0 lbf), preferably at least about 15.568 Newtons (3.5 lbf), more preferably at least about 17.792 Newtons (4 lbf) and most preferably at least about 22.240 Newtons (5 lbf).

In addition, as shown in Table 2, watermelon fruit of the present invention are sweet. Specifically, watermelon fruit display sweetness of at least about 6 brix, more preferably at least about 8 brix and most preferably at least about 10 brix.

TABLE 2

Firmness and sugar content of inbred and hybrid lines developed
from the invention described herein and the PI296341 source.
Firmness readings are in pound force and sugar content is reported
as % Brix. Both measurement methods are described herein.

| Line | Origin | Ploidy | Firmness (Newtons (lbf)) | Sugar content |
| --- | --- | --- | --- | --- |
| PI296341 | USDA collection | Diploid | 60.048 (13.5) | 1.6 |
| 7132 | This invention | Triploid | 20.906 (4.7) | 10.2 |
| 7133 | This invention | Triploid | 27.578 (6.2) | 11.7 |
| 4201 | This invention | Diploid | 35.584 (8.0) | 9.7 |
| 4203 | This invention | Diploid | 34.694 (7.8) | 10.8 |
| 4204 | This invention | Diploid | 28.912 (6.5) | 9.7 |
| 4207 | This invention | Diploid | 28.912 (6.5) | 10 |

Liquid Retention

Figure 2:
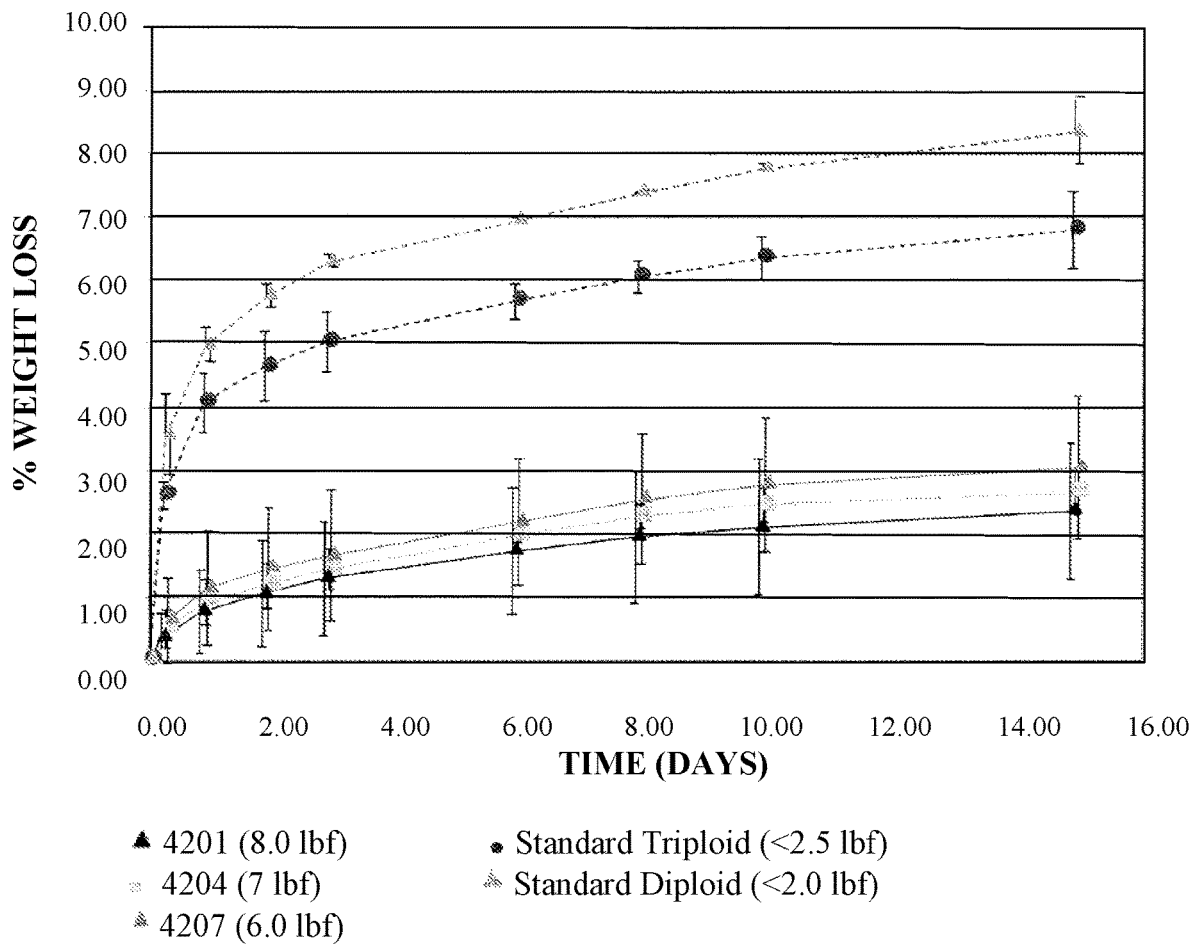
FIG. 2 is a graph showing weight loss after storage at 4° centigrade among processed fruit of standard commercial watermelon varieties and processed fruit of watermelon of the present invention. The weight loss closely approximates liquid leakage from the processed fruit.

The fruit of the present invention also retain liquid better than the fruit of the prior art. Example 4 describes a study that demonstrates this liquid-retaining trait. The study compares liquid leakage rates of cut fruit from watermelon of this invention and of the prior art when stored at 4° centigrade. The results of this study are illustrated in FIG. 2. The study measures percent weight loss over time of cut fruit. This measurement approximates liquid loss, as 95-98% of the weight loss is due to liquid leakage. The remaining weight loss is due to leakage of other components of the fruit, such as soluble solids and acids. The primary conclusion from these data is that processed watermelon fruit of the present invention lose less liquid over time than processed fruit of standard known cultivars.

Watermelon fruit of the present invention lose less than about four percent weight after three days storage at 4° centigrade. Preferably, the fruit of the present invention lose less than about three and one-half percent weight after three days storage at 4° centigrade, more preferably less than about three percent weight, even more preferably less than about two percent weight, and most preferably less than about one and one-half percent weight. Watermelon fruit of the present invention also lose less than about five percent weight after a week of storage at 4° centigrade. Preferably, the fruit of the present invention lose less than about four percent weight after a week of storage at 4° centigrade, more preferably less than about three percent weight, even more preferably less than about two and one-half percent weight.

In addition to having liquid-retaining flesh, the fruit of the present invention are sweet. Specifically, these watermelon fruit display sweetness at least about 6 brix, more preferably at least about 8 brix and most preferably at least about 10 brix.

Other Traits

Watermelon plants of this invention may be seeded or seedless. Methods for obtaining diploid, triploid and tetraploid plants are well known in the art. Specifically, methods for obtaining diploid and triploid watermelon plants and seed of the present invention are described in detail below. Tetraploid plants of the present invention may be easily obtained by those of ordinary skill in the art using known cell biology techniques and the diploid plants described below.

Using standard crossing techniques, those of skill in the art may obtain watermelon fruit of the present invention with desirable traits besides those described above, as the ultra firm flesh and liquid-retaining flesh traits are dominantly inherited. For example, breeders may easily obtain watermelons of the present invention that are of a particular size or have a particular flesh color or rind pattern.

Breeding Techniques—Inbred and Hybrid Lines

Watermelon lines of the present invention were developed in the United States (Georgia, Florida and California), Mexico and Guatemala beginning in the year 2000. Furthermore, watermelon lines were grown for field performance and evaluation of adaptation in Florida, Georgia and California beginning in the year 2003. Additionally, diploid and diploid watermelon hybrids made with lines that produce watermelons having ultra firm flesh and/or liquid-retaining flesh at maturity were evaluated in field conditions in Florida, California and Mexico in 2003 and 2004. Specific crosses and firmness and quality evaluations of resultant fruits are described in detail in the "Examples" section.

For most breeding objectives, commercial breeders work with germplasm that is often referred to as the 'cultivated type'. This germplasm is easier to breed with because it generally performs well when evaluated for horticultural performance. The performance advantage the cultivated types provide is sometimes offset by a lack of allelic diversity. This is the tradeoff a breeder accepts when working with cultivated germplasm—better overall performance, but a lack of allelic diversity. Breeders generally accept this tradeoff because progress is faster when working with cultivated material than when breeding with genetically diverse sources.

In contrast, when a breeder makes either wide intra-specific crosses, or inter-specific crosses, a converse tradeoff occurs. In these examples, a breeder typically crosses cultivated germplasm with a non-cultivated type. In these crosses, the breeder can gain access to novel alleles from the non-cultivated type but has to overcome the genetic drag associated with the donor parent. Because of the difficulty with this breeding strategy, this approach often fails because of fertility or fecundity problems. The difficulty with this breeding approach extends to many crops, and is exemplified with an important disease resistant phenotype that was first described in tomato in 1944 (Smith, Proc. Am. Soc. Hort. Sci. 44:413-416). In this cross, a nematode disease resistance was transferred from *L. peruvianum* (PI128657) into a cultivated tomato. Despite intensive breeding, it was not until the mid-1970s before breeders could overcome the genetic drag and release successful lines carrying this trait. Indeed, even today, tomato breeders deliver this disease resistance gene to a hybrid variety from only one parent. This allows the remaining genetic drag to be masked. The inventiveness of succeeding in this breeding approach has been recognized by the USPTO (U.S. Pat. Nos. 6,414,226, 6,096,944, 5,866,764, and 6,639,132).

In watermelon, the plant introduction (PI) accessions are typically lines that produce small fruits with firm white flesh and very poor taste (even bitter). Even though these lines have such poor horticultural qualities, some watermelon breeders, like some other crop breeders, attempt to breed with these PI lines because they potentially contain novel alleles. To date, the most commonly attempted breeding objective for use of the PI line series is to introgress new disease resistance genes. The process of introgressing novel resistance genes from the PI lines into acceptable commercial types is a long and often arduous process. This process can be difficult because the trait may be polygenic, have low heritability, have linkage drag or some combination of the three.

This breeding project began with a wide cross between cultivated watermelons and PI No. 296341, which was obtained from the USDA collection at the Regional Plant Introduction Station in Griffin, Ga. This accession has been available to watermelon breeders since its deposit into the U.S. Plant Introduction system in 1964.

The original intent of the project, however, was not to make watermelon fruit with firm flesh and/or liquid-retaining flesh. Rather, the original intent of the project was to introgress a resistance to *Fusarium* wilt, specifically to *Fusarium oxysporum* f. sp. *niveum* race 2, referred to herein as FON race 2. Although no commercial watermelons currently contain resistance to FON race 2, the possibility of using PI296341 as a source of resistance has been known for many years (Netzer (1989) Plant Disease 73:518; Martyn and Netzer (1991) HortScience 26:429-432; Wehner et al. (in: Watermelons: Characteristics, production and marketing. Maynard, editor. ASHS Press. Alexandria, Va. (2001)). That there are no watermelon commercial lines for sale with FON race 2 resistance introgressed from PI296341, despite these reports as long as 15 years ago, underscores the difficulty of introgressing traits from wide crosses and creating commercially successful inbreds and hybrids.

In addition to being resistant to FON race 2, PI296341 is characterized by having very small round fruits between 4 and 6 inches in diameter and weighing between 1 and 2.6 pounds. Fruit flesh is white and very firm, with low soluble solids content (Table 2). Organoleptic evaluations of these fruits range from no perception of sweetness to bitter. As described in the "Examples" section below, inbred watermelon plants of the present invention may be obtained by crossing a watermelon with the ultra firm flesh trait and/or liquid-retaining flesh trait (ultra firm parent) with a non-ultra firm flesh watermelon with other desirable quality characteristics, including sweetness (recurrent parent). The ultra firm parent may be plant introduction accession number 296341.

Those of skill in the art will be able to introgress the ultra firm flesh trait and/or the liquid-retaining trait into the recurrent parent by conducting various recurrent backcrosses, selecting for the (i) ultra firm flesh and/or liquid-retaining flesh trait and (ii) the sweetness trait, and finally self-pollinating selected plants of the recurrent backcrosses to create inbred watermelon lines with the above traits. One possible method for accomplishing such introgression is described in the "Examples" section below.

Applicants generated inbred line 3347, which generates sweet ultra firm fruit according to the present invention, using the methods described above and in the "Examples" section. See, especially, Example 5. Inbred line 3347 has been deposited with NCIMB and accorded Accession No. NCIMB 41230. Details of the deposit follow the "Examples" section.

Using known methods, breeders may obtain diploid, triploid and tetraploid inbred lines of watermelon having fruit with the (i) ultra firm flesh and/or liquid-retaining flesh trait and (ii) sweetness trait.

In addition, because the ultra firm flesh and liquid-retaining traits of the present invention are dominantly inherited, breeders may obtain hybrids using the watermelons of this invention. Hybrids may be either diploid or triploid. Specifically, breeders crossed inbred watermelon plants with the above desired flesh traits and sweetness traits to either diploid or tetraploid non-ultra firm flesh cultivars to create, respectively, diploid and triploid watermelon plants with fruit having the ultra firm flesh and/or liquid-retaining flesh trait and sweetness trait. The non-ultra firm flesh parent used in creating a hybrid may also be used to obtain sweet ultra firm flesh and/or liquid-retaining flesh watermelon with other desirable traits, such as a particular size and/or color.

Those skilled in the art recognize that there are several breeding methods used for the introgression of new traits into commercial germplasm, including mass selection, pedigree selection, recurrent selection and backcrossing. By way of example, and by no means limiting, the introgression of ultra firm flesh watermelon fruit at maturity, with high brix levels is described below.

EXAMPLES

Example 1—Generation of F 1 Lines and Backcrosses

In the summer of 2000, four first filial (F1) generation lines were created by crossing 4 Seminis inbred lines as females to PI296341. The four diploid inbred lines used were W-2388, W-1128, W-1119 and W-1488. Line W-2388 is elongated in shape with a length to width (L/W) ratio of 1.8 to 2.2:1. The rind color and pattern is of medium green background with wide darker stripes. This shape and rind pattern phenotype is known to those skilled in the art as an "elongated dark mottle stripe" watermelon fruit. The fruit shape of Line W-1128 is round oval with L/W ratio of 1.0-1.2:1 and rind color is of light to medium green background and narrow darker green stripes. This phenotype is known to those skilled in the art as "round-oval with narrow (or tiger) stripes" watermelon fruit. Fruit shape of Line W-1119 is oval to high round with L/W ratio of 1.1-1.3:1. Rind color is medium green background with wide darker green stripes. This phenotype is known to those skilled in the art as "round-oval dark mottle stripe" watermelon fruit. Fruit of Line W-1488 is of round shape with L/W ratio of 1.0 to 1.1:1. Rind color is light green with some faint mottle/net pattern in the background. This phenotype is known to those skilled in the art as "round gray (or light green)" watermelon fruit. These four lines provide an array of phenotypic diversity amongst the cultivated types.

In the fall of 2000, the respective F1s were used as females to backcross to the above four inbreds, creating the backcross 1 (BC1) generation.

The BC1 generation plants were grown in the spring of 2001, and selections were made based on overall vigor. It was difficult to take the alleles from the PI line into the cultivated types because many of the BC1 and even BC2 plants died. Variation in vine vigor was observed that was associated with survivability. Vine vigor was assumed to be associated with general vigor, and perhaps with pathogen resistance.

The respective BC1 lines, derived from the original four inbreds were crossed as females as follows:
1. [[W-1128×PI296341]F1×W-1128](this is the W-1128 BC1)×W-1128
2. [[W-1119×PI296341]F1×W-1119](this is the W-1119 BC1)×W-1119
3. [[W-1488×PI296341]F1×W-1488](this is the W-1488 BC1)×W-1488
4. [[W-2388×PI296341]F1×W-2388](this is the W-2388 BC1)×W-2068
5. [[W-2388×PI296341]F1×W-2388](this is the W-2388 BC1)×BSI-2543
6. [[W-2388×PI296341]F1×W-2388](this is the W-2388 BC1)×BSI-2527

In these six crosses, the first three were recurrent parent backcrosses. Cross number four was to line W-2068, which is very similar to original parent W-2388. Crosses five and six were to new inbreds. The recurrent backcross program aims to add one or more new traits from the donor parent (in this case, PI296431), while retaining the phenotype of the recurrent parent. However, watermelon breeding is a dynamic process, so it is not uncommon to change the recurrent parent as newer inbred lines are being developed concurrently. Crosses four through six, therefore, were not technically creating the BC2 generation. For clarity in describing the generations, these crosses will be referred to as the BC2* generation. The BC2 and BC2* generation were grown in the summer of 2001. As with the BC1 generation, selection for vine vigor was made. Females thus selected were used to create the BC3 and BC3*generation.
1. W-1128 BC2×W-1128=BC3
2. W-1119 BC2×W-2741=BC3*
3. W-1488 BC2×W-1488=BC3
4. W-2068 BC2*×W-2068=BC3*
5. BSI-2543 BC2*×BSI-2543=BC3*
6. BSI-2527 BC2*×BSI-2527=BC3*

In the fall of 2001, the BC3 and BC3* lines were grown, and selection was again applied for vine vigor. Selected plants were then crossed to create the BC4 and BC4* generations, respectively.
7. W-1128 BC3×W-1128=BC4
8. W-2741 BC3*×W-2741=BC4*
9. W-1488 BC3×W-1488=BC4
10. W-2068 BC3*×W-2068=BC4*
11. BSI-2543 BC3*×BSI-2543=BC4*
12. BSI-2527 BC3*×BSI-2527=BC4*

In addition to selecting for vine vigor, examination of BC3 and BC3* fruit, which contained the BC4 and BC4* generation seed, produced an unexpected finding. Although the BC3 generation still performs poorly when evaluated by current horticultural characteristics, the fruits were examined for quality characteristics. Although most fruit had poor quality, breeder observations as to a small number of fruit included the following: "good fruit color, sweet taste and ultra firm flesh—like an apple." The unexpected finding was that both ultra firm flesh and sweet tasting flesh could be created. The possibility of creating a sweet tasting flesh, combined with ultra firm flesh for the cut fruit segment of the marketplace resulted in a bifurcation of breeding objectives. Applicants initiated a new project with the goal of creating ultra firm flesh watermelon fruits with sweet taste.

Example 2: Self-Pollination of Plants Bearing Ultra Firm Flesh Fruit and Early Flesh Firmness Data In the spring of 2002, the BC4/BC4* generation was grown and evaluated qualitatively for sweet taste, fruit flesh firmness, and horticultural characteristics. Based on these evaluation criteria, plants were selected to create the next generation. Instead of creating another backcross generation, however, each selection from the lines being developed in parallel was self pollinated. The crossing produced the BC4S1/BC4*S1 generation.

In the summer of 2002, the BC4S1/BC4*S1 generation was grown and evaluated qualitatively for sweet taste, fruit flesh firmness, and horticultural characteristics. Based on these evaluation criteria, plants were selected to create the next generation. Self pollination of the selected plants created the BC4S2/BC4*S2 generation.

In the fall of 2002, the BC4S2/BC4S*2 generation was grown and evaluated qualitatively for sweet taste, fruit flesh firmness, and horticultural characteristics. Based on these evaluation criteria, plants were selected to create the next generation. Self pollination of the selected plants created the BC4S3/BC4S*3 generation.

In the spring of 2003 the BC4S3/BC4S*3 generation was grown and evaluated qualitatively for sweet taste, fruit flesh firmness, and horticultural characteristics. Based on these evaluation criteria, plants were selected to create the next generation. Self pollination of the selected plants created the BC4S4/BC4S*4 generation.

For the BC4S3 fruit, both qualitative and quantitative data were obtained for flesh firmness. Specifically, ninety three fruits from individual BC4S3 plants were evaluated for firmness with a penetrometer (model FT011 with an 8 millimeter probe, QA Supplies, Norfolk, Va.). The FT011 penetrometer has a gauge that reads PF, which is an improper abbreviation for pound force. Pound force is a British Engineering measurement scale for pressure, and is properly abbreviated lbf. The conversion from the British measurement system to the International System of Units (SI) is 1 lbf=4.448 newtons. For all flesh firmness measurements using a penetrometer, mature fruits were detached from the plant and cut in an equatorial direction. For orientation, fruits have a stem end and a blossom end. Equatorial slicing means that the fruits are halved such that each half has the blossom end or stem end the farthest distance from the cut site. Samples were taken from the center of the cut fruit. For diploid fruits, sampling occurred inside the seeded ring. Although triploid fruits have few to no seeds, sampling occurred within the same core area of the split fruit. Each half was sampled with the penetrometer, with a total of three to five readings per fruit. Firmness data are reported as an average of the three to five readings.

Even after several generations attempting to fix the firm flesh genotype combined with acceptable horticultural characteristics, including sweetness, FIG. 1 shows that significant fruit flesh firmness variation still existed in these samples. Although the data in FIG. 1 indicate significant variation, it was clear that improvements to fruit firmness had been made. The arrow shows the average firmness rating of the recurrent parents. Even at this early generation in product development, approximately 43% of the fruits have firmness measurements of not less than 17.792 Newtons (4 lbf).

Some phenotypes are determined by the genotype at one locus. These simple traits, like those studied by Mendel, fall in discontinuous categories such as green or yellow seeds. Most variation observed in nature, however, is continuous, like yield in field corn, or human blood pressure. FIG. 1 shows a continuous-type pattern of firm flesh variation, similar to a normal distribution. Unlike simply inherited traits, continuous variation can be the result of polygenic inheritance. Loci that affect continuous variation are referred to as quantitative trait loci, or QTLs. Variation in the phenotype of a quantitative trait is the result of the allelic composition at the QTLs and an environmental effect. Applicants identified several potential causes for the variation: (1) the fruit firmness trait may be controlled by several to many QTLs; (2) the fruit firmness trait may be caused by one or a few genes, but have a low heritability; and (3) the trait may be both polygenic and have low heritability. Those skilled in the art recognize that the marketplace requires product uniformity. Thus, the utility of the invention is higher for those traits with high heritability that are not greatly affected by the environment. The heritability of a trait is the proportion of the phenotypic variation attributed to the genetic variance. This ratio varies between 0 and 1. Thus, a trait with heritability near 1.0 is not greatly affected by the environment. Because the fruit firmness variation shown in FIG. 1 did not explain the cause of the variation, further experiments were conducted, as described in the examples below, to determine the cause of the variation.

Example 3: Generation of Diploid Hybrids with Ultra Firm Flesh Trait

In the fall of 2002, in addition to the self pollinations, crosses with selected BC4S2/BC4S*2 generation plants were made to other commercial inbreds that do not contain the ultra firm flesh phenotype. These crosses were made to test to what extent the ultra firm flesh trait would be dominantly inherited in a hybrid combination. Those skilled in the art will recognize the importance of establishing how well traits developed in inbred lines function in a hybrid combination.

In the spring of 2003, these test hybrids were evaluated in Florida and California. Although many hybrid combinations were tested in these trials, most of these data are not shown. Instead, data from four top performing hybrids across two trialing locations are shown in Tables 3 and 4. Hybrids were evaluated by a number of criteria, including the rind color pattern. For these hybrids, all had a mottled stripe pattern, designated MS. Also evaluated were fruit length and width, rind thickness, flesh color, firmness and sweetness levels.

When determining sweetness levels quantitatively, Applicants used a refractometer to measure brix levels. Specifically, brix levels were measured with a digital, hand-held refractometer (Leica Microsystems model AR200, Reichert Inc., Depew, N.Y.) according to manufacturer's instructions. Brix levels were determined after the penetrometer firmness readings, by squeezing a sampled fruit until drops of liquid fell into the well of the refractometer. One brix measurement was taken from each half of a cut fruit, and the data were recorded as an average.

Tables 3 and 4 show that the test hybrids do exhibit small variation between the test sites. Taken together, however, the data show that these top performing hybrid combinations performed uniformly in the two locations. In particular, these hybrids consistently had ultra firm flesh, as measured by pound force of pressure and very good soluble solids, as measured by percentage brix.

Fruit flesh firmness data across the two locations provided insight into the genetics of the trait, answering questions as to heritability posed by the data shown in FIG. 1. First, these data show that the ultra firm flesh trait can be delivered into an F1 hybrid from a single parent. In other words, genetic loci selected in the method described herein affect fruit firmness in a dominant manner. This is a critical fact for the design of breeding strategies. Moreover, consistency in the firmness measurements across several hybrids in the two locations show that the ultra firm flesh alleles selected in the method described herein have a high heritability. Those skilled in the art recognize the importance of creating commercial lines with highly heritable horticultural traits. Specifically, such cultivars will allow growers to produce a crop with uniform market specifications.

TABLE 3

Test hybrid evaluations: Florida, Spring 2003

| Hybrid | Rind | Length (cm) | Width (cm) | Rind Thickness (cm) | Flesh Color | Firmness (Newtons (lbf)) | Sweetness (Brix) |
|---|---|---|---|---|---|---|---|
| 4201 | MS | 23 | 19.5 | 1.5 | Red | 35.584 (8.0) | 9.7 |
| 4203 | MS | 25.5 | 21.5 | 1.5 | Red | 33.360 (7.5) | 11.3 |
| 4204 | MS | 23 | 19 | 1.0 | Red | 26.688 (6.0) | 9.3 |
| 4207 | MS | 25 | 20 | 2.0 | Red | 31.136 (7.0) | 9.6 |

TABLE 4

Test hybrid evaluations: California, Spring 2003

| Hybrid | Rind | Length (cm) | Width (cm) | Rind Thickness (cm) | Flesh Color | Firmness (Newtons (lbf)) | Sweetness (Brix) |
|---|---|---|---|---|---|---|---|
| 4201 | MS | 22.5 | 17 | 1.5 | Red | 35.584 (8.0) | 9.7 |
| 4203 | MS | 23 | 17 | 1.5 | Red | 35.584 (8.0) | 10.3 |
| 4204 | MS | 25 | 18 | 2.0 | Red | 31.136 (7.0) | 10.0 |
| 4207 | MS | 25 | 17 | 1.5 | Red | 26.688 (6.0) | 10.3 |

Example 4: Evaluation of Liquid-Retaining Flesh Characteristics of Ultra Firm Flesh Hybrids As described herein, studies agree that minimally processed products have a short shelf life of 2 to 3 days maximum (Perkins-Veazie et al. (1998) Hortscience 33:605; Wehner et al. (in: Watermelons: Characteristics, Production and Marketing. Maynard, editor. ASHS Press, Alexandria, Va. (2001)). Although the maximum shelf life of cut watermelon fruits is only a few days, product quality begins to deteriorate rapidly after being processed. In cut products presented in plastic food containers, the consumer can see this rapid deterioration because liquid will leak out of the cut products and accumulate in the bottom of the container.

Mature fruits from the 2003 California hybrid trial (Example 3, Table 4) were evaluated for leakage using a liquid retention test as described herein (see FIG. 2). This test was performed at 4° centigrade. Fruits from test hybrids 4201, 4204 and 4207 were tested along with standard diploid and triploid hybrid controls. Test hybrids had the ultra firm flesh trait, with firmness readings of 35.584 Newtons (8.0 lbf), 31.136 Newtons (7.0 lbf) and 26.688 Newtons (6.0 lbf), respectively (Table 4). Controls had flesh firmness readings of <8.896 Newtons (2.0 lbf) and <11.120 Newtons (2.5 lbf), respectively. To measure liquid loss, the edible portion of the fruits were cut into approximately 1" cubes and weighed. The approximate 1" cube size was chosen because this best approximates the processed product size found in retail outlets. Over a 16 day period, samples were re-weighed, and the liquid loss was estimated by calculating the percent weight loss.

FIG. 2 graphically displays the percent weight loss of these samples over a 16 day period. Multiple samples per line were tested; the triangles, circle and squares represent the mean values at each time point, and the sample standard deviations are shown as bars. Data in FIG. 2 show large differences in weight losses between the controls having softer fruit flesh and the fruits with the ultra firm flesh trait. The difference between the controls and the test hybrids with the ultra firm flesh phenotype was apparent by the first time point, which was approximately 6½ hours after the samples were cut. Therefore, although cut product from standard cultivars may have a shelf life of up to 2 to 3 days, product deterioration begins almost immediately after they are cut. These data show that the ultra firm flesh lines developed using the method described herein will resist the rapid liquid leakage now common in cut watermelon fruits. Because these ultra firm flesh fruits will retain liquid once cut, they will last longer in the minimally processed watermelon market.

Example 5: Final Self Pollination and Creation and Evaluation of Triploid Hybrids In the summer of 2003, the BC4S4/BC4S*4 generation, the generation of which is described above in Example 2, was grown and evaluated qualitatively for sweet taste, fruit flesh firmness, and horticultural characteristics. Based on these evaluation criteria, plants were selected to create the next generation. Self pollination created the BC4S5/BC4S*5 generation.

In the fall of 2003, the BC4S5/BC4S*5 generation was grown and evaluated qualitatively for sweet taste, fruit flesh firmness, and horticultural characteristics. Based on these evaluation criteria, plants were selected to create the next generation. Self pollination created the BC4S6/BC4S*6 generation.

In addition, quantitative firmness data were collected from the BC4S5 generation for lines that were qualitatively sweet. Specifically, twenty six lines were tested, and results are shown below in Table 5. Fourteen of these lines had a single fruit tested, and the remaining 12 lines had 2 or 3 fruits tested per line. The range of firmness amongst the twenty six lines ranged from a low of 17.792 Newtons (4.0 lbf) to a high of 35.584 Newtons (8.0 lbf). For the lines that had multiple samples, 11 of the 12 lines showed no difference in the penetrometer measurements. One line did show a penetrometer measurement difference of 4.448 Newtons (1 lbf). These data provide further insight as to questions raised by FIG. 1, which showed variation in the ultra firm flesh trait in the BC4S3 generation. In particular, it was unclear in the BC4S3 generation whether the ultra firm flesh trait displayed a low or high heritability. That many lines developed in parallel gave elevated, but different fruit firmness readings suggested that the ultra firm flesh is polygenic in nature. The very low intra-line variation shown in Table 5, together with the test hybrid data shown in Tables 3 and 4 demonstrate that the ultra firm flesh trait has a high heritability. Those skilled in the art recognize the importance of creating commercial lines with highly heritable horticultural traits because such cultivars allow growers to produce a crop with uniform market specifications.

Table 5 shows the inbred line evaluations from the BC4S5/BC4S*5 generation.

| Line-replication no. | Firmness (Newtons (lbf)) |
|---|---|
| 3333-1 | 31.136 (7.0 lbf) |
| 3333-2 | 35.584 (8.0 lbf) |
| 3334-1 | 22.240 (5.0 lbf) |
| 3334-2 | 22.240 (5.0 lbf) |
| 3335-1 | 35.584 (8.0 lbf) |
| 3335-2 | 35.584 (8.0 lbf) |
| 3336-1 | 22.240 (5.0 lbf) |
| 3336-2 | 22.240 (5.0 lbf) |
| 3337-1 | 22.240 (5.0 lbf) |
| 3339-1 | 17.792 (4.0 lbf) |
| 3340-1 | 20.016 (4.5 lbf) |
| 3340-2 | 20.016 (4.5 lbf) |
| 3340-3 | 20.016 (4.5 lbf) |
| 3341-1 | 22.240 (5.0 lbf) |
| 3346-1 | 22.240 (5.0 lbf) |
| 3346-2 | 22.240 (5.0 lbf) |
| 3347-1 | 26.688 (6.0 lbf) |
| 3347-2 | 26.688 (6.0 lbf) |
| 3347-3 | 26.688 (6.0 lbf) |
| 3348-1 | 26.688 (6.0 lbf) |
| 3348-2 | 26.688 (6.0 lbf) |
| 3348-3 | 26.688 (6.0 lbf) |
| 3349-1 | 22.240 (5.0 lbf) |
| 3350-1 | 22.240 (5.0 lbf) |
| 3350-2 | 22.240 (5.0 lbf) |
| 3350-3 | 22.240 (5.0 lbf) |
| 3352-1 | 24.464 (5.5 lbf) |
| 3353-1 | 26.688 (6.0 lbf) |
| 3355-1 | 35.584 (8.0 lbf) |
| 3355-2 | 35.584 (8.0 lbf) |
| 3357-1 | 22.240 (5.0 lbf) |
| 3357-2 | 22.240 (5.0 lbf) |
| 3358-1 | 22.240 (5.0 lbf) |
| 3358-2 | 22.240 (5.0 lbf) |
| 3359-1 | 26.688 (6.0 lbf) |
| 3378-1 | 31.136 (7.0 lbf) |
| 3380-1 | 31.136 (7.0 lbf) |
| 3384-1 | 31.136 (7.0 lbf) |
| 3386-1 | 31.136 (7.0 lbf) |
| 3387-1 | 35.584 (8.0 lbf) |
| 3388-1 | 31.136 (7.0 lbf) |
| 3390-1 | 26.688 (6.0 lbf) |
| 3390-2 | 26.688 (6.0 lbf) |
| 3392-1 | 35.584 (8.0 lbf) |
| 3392-2 | 35.584 (8.0 lbf) |
| 3394-1 | 24.464 (5.5 lbf) |
| 3394-2 | 24.464 (5.5 lbf) |
| 3396-1 | 31.136 (7.0 lbf) |
| 3396-2 | 31.136 (7.0 lbf) |
| 3397-1 | 31.136 (7.0 lbf) |
| 3397-2 | 31.136 (7.0 lbf) |
| 3398-1 | 33.360 (7.5 lbf) |
| 3399-1 | 33.360 (7.5 lbf) |
| 3399-2 | 33.360 (7.5 lbf) |
| 3400-1 | 33.360 (7.5 lbf) |
| 3401-1 | 33.360 (7.5 lbf) |
| 3401-2 | 33.360 (7.5 lbf) |
| 1577-1 | 35.584 (8.0 lbf) |

-continued

| Line-replication no. | Firmness (Newtons (lbf)) |
|---|---|
| 1577-2 | 35.584 (8.0 lbf) |
| 1577-3 | 35.584 (8.0 lbf) |
| 1577-4 | 35.584 (8.0 lbf) |
| 1577-5 | 35.584 (8.0 lbf) |
| 1577-6 | 35.584 (8.0 lbf) |
| 1577-7 | 35.584 (8.0 lbf) |

In addition to the self pollinations described above, crosses with selected BC4S4/BC4S*4 generation plants were made to other commercial tetraploid inbreds that do not contain the ultra firmness phenotype. These tetraploid× diploid crosses were made to test to what extent the ultra firm flesh trait would be dominantly inherited in a triploid hybrid combination. As shown in Table 6 below, the ultra firm flesh trait was inherited by the triploid seedless fruit.

TABLE 6

Mature fruit flesh firmness and sweetness scores. Firmness was measured as described herein with a penetrometer.

| Hybrid | Rind | Length (cm) | Width (cm) | Rind Thickness (cm) | Flesh Color | Firmness (Newtons (lbf)) | TSS (Brix) |
|---|---|---|---|---|---|---|---|
| SVR8034-7131 | TS | 28 | 24 | 1.2 | Red | 22.240 (5.0) | 10.2 |
| SVR8034-7132 | MS | 26 | 25 | 1.0 | Red | 17.792 (4.0) | 9.7 |
| SVR8034-7133 | MS | 28 | 26 | 1.0 | Red | 22.240 (5.0) | 10.5 |
| SVR8034-7134 | MS | 26 | 24 | 1.1 | Red | 20.016 (4.5) | 10.0 |

All references cited herein are hereby expressly incorporated herein by reference.

DEPOSIT INFORMATION

A deposit of the Seminis Vegetable Seeds proprietary inbred and hybrid watermelon line 3347 disclosed above and recited in the appended claims has been made with NCIMB Ltd, 23 St. Machar Drive, Aberdeen AB24 3RY. The date of the deposit was 1 Jul. 2004. The deposit of 2500 seeds for this variety were taken from the same deposit maintained by Seminis Vegetable Seeds since prior to the filing date of this application. Upon issuance of a patent, all restrictions upon the deposit will be removed, and the deposit is intended to meet all of the requirements of 37 C.F.R. § 1.801-1.809. The NCIMB accession number for inbred line 3347 was deposited as Accession No. NCIMB 41230.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method for producing a watermelon plant that produces a mature fruit having flesh that resists pressure of at least 3.5 pounds force (lbf) and soluble solids of at least 6 brix comprising:
   a. crossing a first watermelon variety comprising soluble solids of not less than 8 brix with a second watermelon variety comprising mature fruit flesh that resists pressure of at least 3.5 lbf;
   b. performing at least one backcross with said first watermelon variety or said second watermelon variety, and
   c. performing one or more cycles of self-pollination of products of the backcross of step (b) or one or more recurrent backcrosses with said first watermelon variety or said second watermelon variety, wherein the progeny of said crosses, backcrosses, or self-pollination are selected for soluble solids of not less than 8 brix, flesh that resists pressure of at least 3.5 lbf, or both.

2. The method of claim 1, wherein said second watermelon variety comprises flesh that resists pressure of at least 4.0 lbf.

3. The method of claim 2, wherein said progeny are selected for flesh that resists pressure of at least 4.0 lbf.

4. The method of claim 1, wherein said first watermelon variety has soluble solids of at least 10 brix.

5. The method of claim 1, wherein said performing step c comprises self-pollination.

6. The method of claim 1, wherein said performing step c comprises recurrent back-crosses with said first watermelon variety.

7. The method of claim 1, wherein said performing step c comprises recurrent back-crosses with said second watermelon variety.

8. The method of claim 1, wherein said first watermelon variety is a commercial line.

* * * * *